(12) United States Patent
Kennedy, II et al.

(10) Patent No.: US 8,109,872 B2
(45) Date of Patent: Feb. 7, 2012

(54) ENDOSCOPIC APPARATUS HAVING AN IMPROVED CATHETER

(75) Inventors: Kenneth C. Kennedy, II, Clemmons, NC (US); Vihar C. Surti, Winston-Salem, NC (US); David F. Waller, Tampa, FL (US)

(73) Assignee: Cook Medical Technologies LLC, Bloomington, IN (US)

( * ) Notice: Subject to any disclaimer, the term of this patent is extended or adjusted under 35 U.S.C. 154(b) by 1125 days.

(21) Appl. No.: 11/713,940

(22) Filed: Mar. 5, 2007

(65) Prior Publication Data

US 2007/0208221 A1 Sep. 6, 2007

(51) Int. Cl.
*A61B 1/00* (2006.01)
*A61B 1/04* (2006.01)

(52) U.S. Cl. .................. 600/107; 600/117; 600/129

(58) Field of Classification Search .................. 600/106, 600/107, 104, 117, 129
See application file for complete search history.

(56) References Cited

U.S. PATENT DOCUMENTS

| | | | |
|---|---|---|---|
| 4,407,273 A | 10/1983 | Ouchi et al. | |
| 4,841,949 A | 6/1989 | Shimizu et al. | |
| 5,343,853 A | 9/1994 | Komi et al. | |
| 5,358,493 A * | 10/1994 | Schweich et al. | 604/264 |
| 5,386,818 A | 2/1995 | Schneebaum et al. | |
| 5,456,680 A * | 10/1995 | Taylor et al. | 606/2 |
| 5,707,344 A | 1/1998 | Nakazawa et al. | |
| 5,820,546 A | 10/1998 | Ouchi | |
| 5,871,475 A * | 2/1999 | Frassica | 604/264 |
| 5,899,850 A | 5/1999 | Ouchi | |
| 5,921,971 A | 7/1999 | Agro et al. | |
| 5,938,586 A | 8/1999 | Wilk et al. | |
| 5,938,587 A | 8/1999 | Taylor et al. | |
| 5,976,075 A * | 11/1999 | Beane et al. | 600/146 |
| 5,989,230 A * | 11/1999 | Frassica | 604/264 |
| 6,010,464 A * | 1/2000 | Galdonik et al. | 600/585 |
| 6,613,002 B1 * | 9/2003 | Clark et al. | 600/593 |
| 6,827,683 B2 | 12/2004 | Otawara | |
| 7,063,659 B2 * | 6/2006 | Goto et al. | 600/104 |
| 7,087,010 B2 * | 8/2006 | Ootawara et al. | 600/104 |
| 2002/0091303 A1 | 7/2002 | Ootawara et al. | |
| 2003/0100818 A1 * | 5/2003 | Lei et al. | 600/117 |
| 2005/0101836 A1 | 5/2005 | Onuki et al. | |
| 2006/0173241 A1 * | 8/2006 | Ouchi et al. | 600/129 |

FOREIGN PATENT DOCUMENTS

| | | |
|---|---|---|
| EP | 1 764 028 A1 | 3/2007 |
| WO | WO 99/29362 | 6/1999 |
| WO | WO 00/74565 A1 | 12/2000 |
| WO | WO 2006/004053 A1 | 1/2006 |
| WO | WO 2006/113465 A1 | 10/2006 |

OTHER PUBLICATIONS

International Search Report—PCT/US2007/005564 (Jan. 21, 2008).
International Search Report—PCT/US2007/005657 (Sep. 13, 2007).
International Search Report—PCT/US2007/005859 (Nov. 16, 2007).

* cited by examiner

*Primary Examiner* — Anhtuan Nguyen
*Assistant Examiner* — Alireza Nia
(74) *Attorney, Agent, or Firm* — Brinks Hofer Gilson & Lione (57) ABSTRACT

A delivery apparatus cooperable with a grasping slot of an elevator of endoscope for enhanced delivery to a target location in a patient is disclosed. The apparatus comprises a catheter including an inner lumen and an outer surface. The outer surface has a projection formed thereon. The projection radially extends from the outer surface. The projection is configured to receive the elevator for enhanced delivery in the patient.

16 Claims, 7 Drawing Sheets

ENDOSCOPIC APPARATUS HAVING AN IMPROVED CATHETER

CROSS-REFERENCE TO RELATED APPLICATIONS

This application claims the benefit of U.S. Provisional Application Ser. No. 60/778,813, filed on Mar. 3, 2006, entitled "ENDOSCOPIC APPARATUS HAVING A CATHETER WITH LATERAL PROJECTIONS FOR ENHANCED DELIVERY," the entire contents of which are incorporated herein by reference.

This application claims the benefit of U.S. Provisional Application Ser. No. 60/779,244, filed on Mar. 3, 2006, entitled "ENDOSCOPIC APPARATUS HAVING A ROTARY CATHETER COOPERABLE WITH AN ENDOSCOPIC ELEVATOR," the entire contents of which are incorporated herein by reference.

This application claims the benefit of U.S. Provisional Application Ser. No. 60/779,549, filed on Mar. 6, 2006, entitled "ENDOSCOPIC APPARATUS HAVING LONGITUDINAL RIDGE FOR ENHANCED DELIVERY," the entire contents of which are incorporated herein by reference.

BACKGROUND OF THE INVENTION

The present invention relates to medical devices, and more particularly, to components cooperable with endoscopes having an elevator.

Endoscopic devices have been commonly used for various procedures, typically in the abdominal area. Endoscopy is the examination and inspection of the interior of body organs, joints or cavities through an endoscope. Endoscopy allows physicians to peer through the body's passageways. An endoscopic procedure may be used to diagnose various conditions by close examination of internal organ and body structures and may also guide therapy and repair, such as the removal of torn cartilage from the bearing surfaces of a joint. A biopsy, a procedure involving tissue sampling for pathologic testing, may also be performed under endoscopic guidance. For example, endoscopic procedures include the following known procedures: gastroscopy, sigmoidoscopy and colonoscopy, esophago gastro duodenoscopy (EGD), endoscopic retrograde cholangiopancreatography (ERCP), and bronchoscopy.

The use of endoscopic treatments has recently increased for some diseases occurring in the gastrointestinal or pancreatobiliary duct systems. Endoscope systems are used frequently for diagnostic procedures, including contrast imaging of biliary or pancreatic ducts. Endoscopes are also used in procedures for retrieving gallstones that exist in the common bile duct and elsewhere.

Typically, these treatments are performed in the pancreatic duct, bile duct, and the hepatic duct by positioning the distal end of an endoscope in the vicinity of the duodenal papilla. Once the endoscope is in place, a wire guide is delivered to the target anatomy via the working channel of the endoscope. In order to guide the wire guide (or other medical instruments) out of the working channel of the endoscope, a rigid elevator is typically used to orient or deflect the distal end of the wire guide. When the distal end of the wire guide is oriented, the wire guide is inserted into the target anatomy. At this point in the procedure, a catheter or similar treatment instrument can be passed over the wire guide either in a conventional over-the-wire style to the target anatomy.

Often, and in particular, during ERCP procedures, there is a need to precisely control the orientation of the device (e.g., catheter or wire) in the anatomy of a patient. One notable example of this requirement is the need, during ERCP, to orient an electrocautery sphincterotome with its cutting wire towards the superior margin of the papillary orifice in order to reduce the chances of cutting the wall of the duodenum of the pancreatic duct. One of the more common means of controlling orientation of such a device in the patient anatomy is to control the device orientation with respect to the endoscope as the device exits the working channel. This can often be accomplished during ERCP procedures because the endoscope is usually held in one of two positions in the patient anatomy. For both positions, the superior margin of the papillary orifice is typically oriented laterally adjacent or at a "twelve-o'clock" position relative the endoscopic view. Thus, if a sphincterotome can repeatably and reliably exit the endoscope working channel with its cutting wire oriented at the twelve-o'clock position, the cutting wire could be more precisely oriented in the patient anatomy.

Additionally, other medical devices such as catheters are disposed through the working channel of an endoscope for various treatments and procedures wherein an elevator is used to position the device at a target location in the patient anatomy. Current endoscopes with elevators simply actuate or lift the elevator relative to the distal tip of an insertion tube to move the device from one location to another. However, there is a need to incrementally and relatively precisely move the device further from the distal tip of the insertion tube after actuation of the elevator.

Moreover, as diagnostic and therapeutic procedures progress, various devices are withdrawn from, or are introduced into the patient, via the wire guide. This swapping of devices over the wire is known as an exchange, and several exchanges may occur during a single endoscopy procedure.

An aspect of successful exchanges is maintaining the position of the wire guide within the patient. The position of the endoscope does not often change appreciably once procedures have started. One way of maintaining wire guide access during exchanges is to temporarily anchor the wire to the endoscope. As such, recent developments in the market include wire locking devices that attach to the handle portion of the endoscope in the region of the inlet to the device channel. This affords the clinician the opportunity of directly locking the wire to the endoscope. In new developments, some endoscopes may be utilized to lock the wire to the endoscope at its distal tip within the patient. This gives the clinician the ability to lock the wire to the endoscope indirectly by activating the elevator. However, there is a concern of wedging the device, e.g., catheter and wire, within the endoscope since the locking would occur inside the patient and outside the view of the endoscope. Thus, there is a need to minimize wedging or unintended locking of a medical device, e.g., a catheter or a wire guide, when used within an endoscope while maintaining position of the medical device within the patient anatomy.

BRIEF SUMMARY OF THE INVENTION

The present invention generally provides an endoscopic system and an endoscopic delivery apparatus that solve the challenges mentioned above. The present invention provides a way of precisely controlling the orientation and delivering the device with respect to the anatomy during endoscopy while avoiding wedging or unintended locking of the medical device at the distal tip of the endoscope.

For example, the present invention generally provides a delivery apparatus cooperable with a grasping slot of an elevator of endoscope for delivery to a target location in a patient. The apparatus comprises a catheter including an inner lumen and an outer surface having a projection formed thereon. The projection radially extends from the outer surface. The projection is configured to receive the elevator for enhanced delivery in the patient.

In one embodiment, the projection is at least one pair of projections circumferentially formed on the outer surface in longitudinal relationship with and spaced apart from each other. The at least one pair of projections radially extends from the outer surface of the catheter. The at least one pair of projections defining an anchor area in which the elevator is to be received for temporary longitudinal fixation of the catheter.

In another embodiment, the projection is a rotary member formed helically on the outer surface. The rotary member is cooperable with the grasping slot for the elevator, wherein rotation of the catheter within the grasping slot incrementally moves the catheter relative to the target location.

In still another embodiment, the projection is a self-orienting ridge formed longitudinally along the outer surface of the catheter. The self-orienting ridge is cooperable with the grasping slot of the elevator. The ridge is configured to be received in the grasping slot to inhibit rotation of the catheter with respect to the elevator.

In another example, the present invention provides an endoscopic system having enhanced features for delivering a medical device in a patient. The system comprises an insertion tube that extends to a distal tip including an elevator movably attached thereto. The elevator has an inner side formed therethrough defining a grasping slot. The system further comprises a catheter including an inner lumen and an outer surface having a projection formed thereon. The projection radially extends from the outer surface. The projection is configured to receive the elevator for enhanced delivery in the patient.

In yet another example, the present invention provides a method of anchoring an apparatus cooperable with an elevator of an endoscope for enhanced delivery in a patient. The method comprises inserting the catheter mentioned above in a patient anatomy. The method further comprises positioning the catheter within a target location in the patient anatomy and engaging the projections with the elevator to receive the elevator in the anchor area for temporary longitudinal fixatation of the catheter.

Further objects, features, and advantages of the present invention will become apparent from consideration of the following description and the appended claims when taken in connection with the accompanying drawings.

DETAILED DESCRIPTION OF THE INVENTION

Embodiments of the present invention provide an endoscopic system and an endoscopic delivery apparatus that allows for a temporary way of maintaining longitudinal or radial position of a delivery apparatus while delivering a medical device, e.g., a catheter, to a target location within a patient. For example, in one embodiment, an outer catheter has projections radial extending therefrom at the distal portion of the catheter. The projections define anchor areas that are configured to cooperate and receive the inner side of an elevator of an endoscope so that the clinician may temporarily maintain longitudinal position of the delivery apparatus during endoscopy. Once a minimal bending force is reached, the projections bend or fold when the catheter is retracted or moved forward, allowing longitudinal movement of the catheter.

Figure 1A:
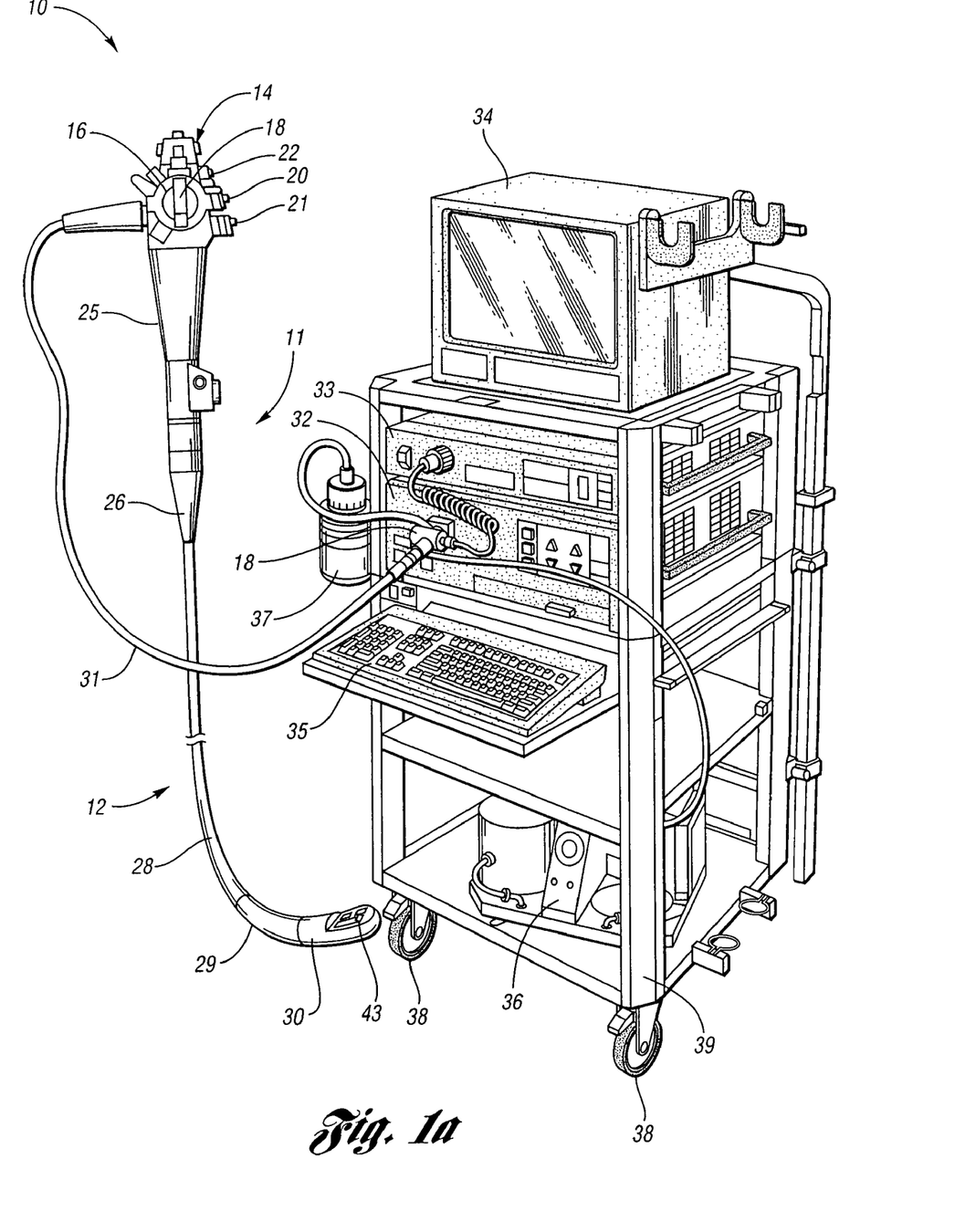
FIG. 1a is a perspective view of an endoscopic system comprising an endoscope in accordance with one embodiment of the present invention.
Figure 1B:
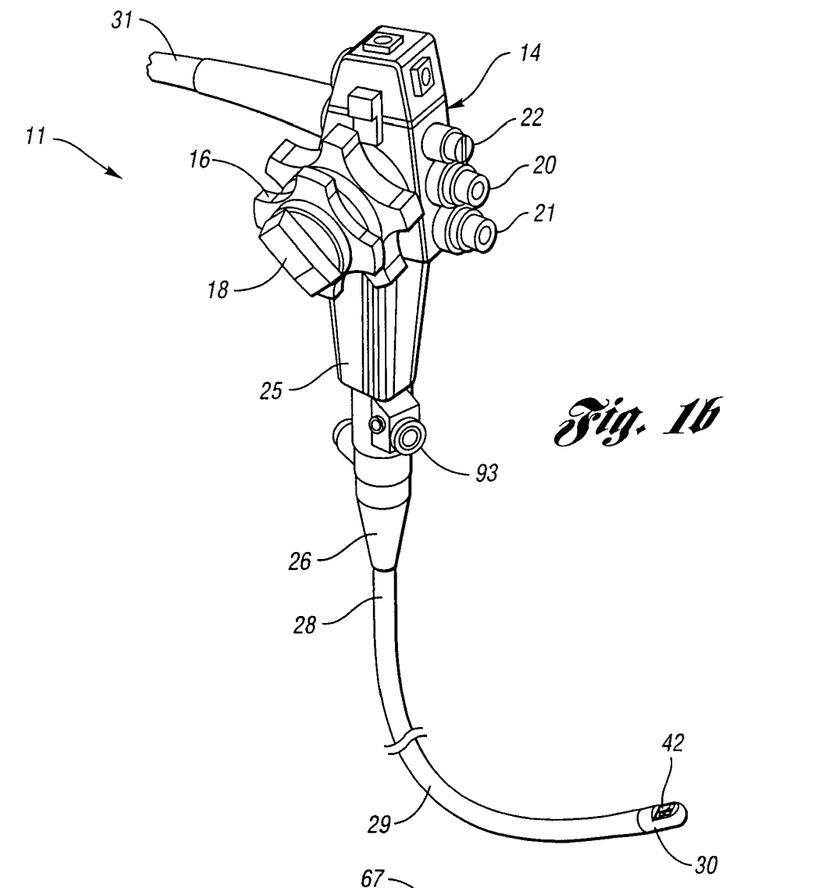
FIG. 1b is a perspective view of the endoscope depicted in FIG. 1A.
Figure 1C:
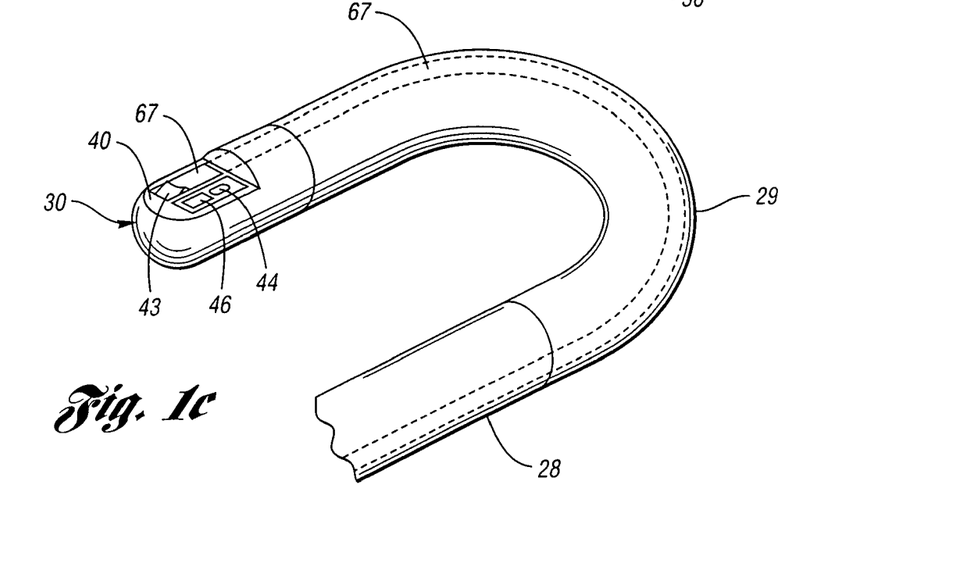
FIG. 1c is an elevated view of a distal tip of the endoscope in accordance with one embodiment of the present invention.
Figure 2:
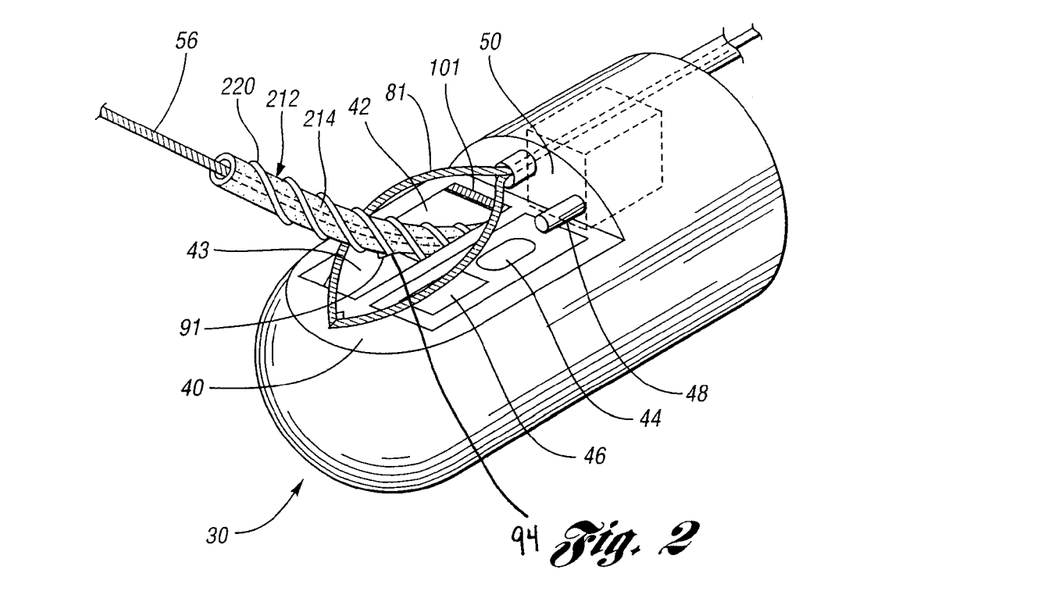
FIG. 2 is an enlarged view of the distal tip of the endoscope in accordance with one embodiment of the present invention.
Figure 3:
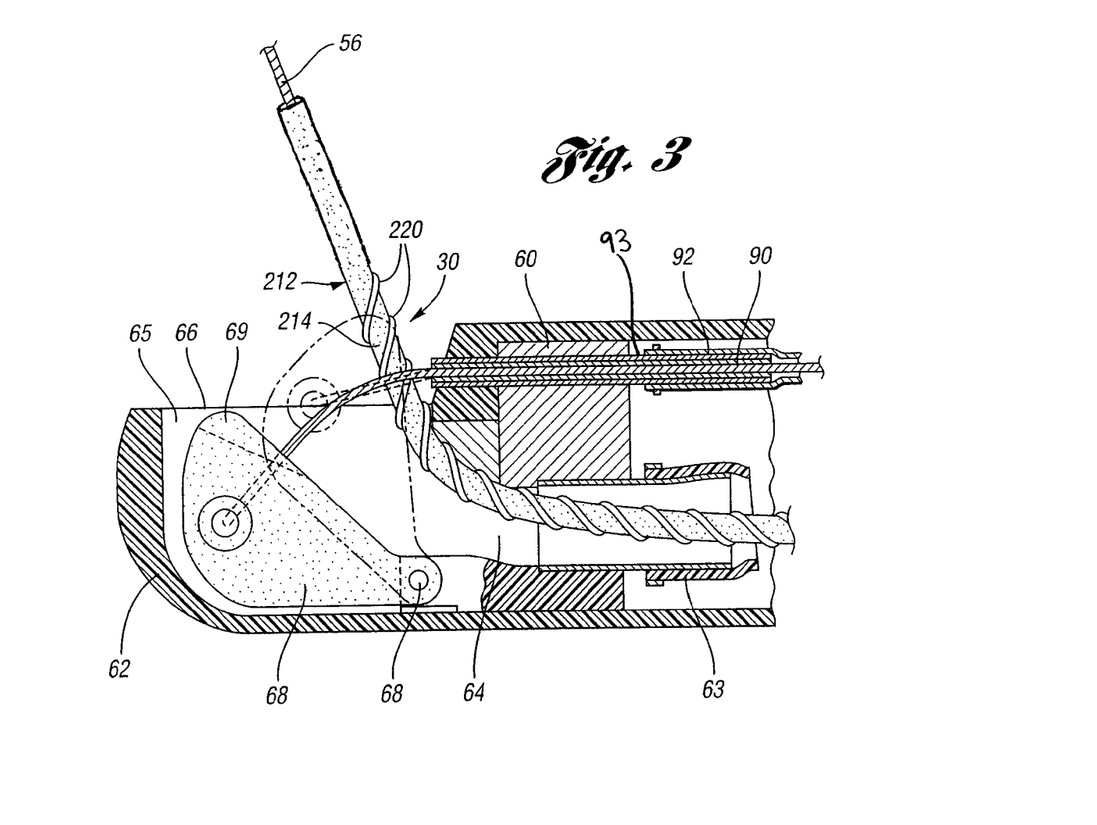
FIG. 3 is a cross-sectional view of the distal tip of the endoscope insertion portion of the endoscope taken along line 3-3.

FIGS. 1-3 illustrate an endoscopic system comprising an endoscope having an elevator with a distal tip. In one example, this system represents a modification to the Olympus V-Scope™. Additional details relating to the endoscopic system discussed herein are described in U.S. Pat. No. 6,827, 683, entitled "ENDOSCOPE SYSTEM AND MEDICAL TREATMENT METHOD" issued Dec. 7, 2004 to Takashi Otawara, which is incorporated herein by reference in its entirety.

FIG. 1a illustrates an endoscopic system 10 comprising an endoscope 11 in accordance with one embodiment of the present invention. In this embodiment, the endoscope 11 comprises an insertion tube 12 to be inserted into a body cavity for various endoscopic procedures including gastroscopy, sigmoidoscopy and colonoscopy, esophago gastro duodenoscopy (EGD), endoscopic retrograde cholangiopancreatography (ERCP), and bronchoscopy. The insertion tube 12 has a channel port through which endoscopic units may be disposed. In one embodiment, endoscopic units disposed in one of the ports may include one embodiment of an improved elevator having a distal tip.

As shown in FIGS. 1a and 1b, the endoscope 11 further includes a control system 14 that is in mechanical and fluid communication with the insertion tube 12. The control system 14 is configured to control the insertion tube 12 and endoscopic parts disposed therein. As shown, the control system 14 includes first and second control knobs 16, 18. The control knobs 16, 18 are configured to be in mechanical communication with the insertion tube 12. The control knobs 16, 18 allow the physician to control and guide, by known means, the insertion tube 12 through vessels and cavities of a patient. The control system 14 further includes valve switches (e.g., suction valve 20, air/water valve 21, camera valve 22), each of which are in communication with one of the channel ports 13 of the insertion tube 12. For example, the suction valve switch 20, when activated, allows a vacuum from a suction source through a suction channel port for suctioning unwanted plaque and debris from the patient. In one example, the distal end of the insertion tube 12 is inserted, rectally or orally, to a predetermined endoscopic location within a patient. Insertion of the insertion tube 12 may be rectally or orally depending on the endoscopic procedure. The endoscope, in combination with the elevator having the distal tip, reduces the risk of tearing or scraping of the wire guide.

In this embodiment, the insertion tube 12 comprises an operating portion 25 connected to the control system 14 and extending to an insertion protecting member 26. A control system 14 is connected to the operating portion 25 and is configured to control the insertion tube 12. In this embodiment, the insertion tube 12 is composed of components that include a flexible tube 28, a flexure 29 connected to the flexible tube 28, and an endoscope tip 30 connect to the flexure 29. A universal cord 31, on one end, is connected and in communication with the control system 14. On the other end, the cord 31 has a connector 18 attached thereto. The connector 18 is in communication to a light guide tube and electrical contact, and is connected to a light source apparatus 32 and an image processing apparatus 33 (external devices). These external devices may include a monitor 34, an input keyboard 35, a suction pump apparatus 36, irrigation bottle 37, and other suitable apparatus that are installed on a rack 39 equipped with rollers 38.

As shown in FIGS. 1c and 2, a cutout 40 is formed on the outer circumferential surface of the tip 30. In this embodiment, a channel opening 42 is formed on one side of the cutout 40, and an objective lens 44 and a light source 46 are disposed on another side of the cutout 40 for imaging. Both the objective lens 44 and the light source 46 are positioned adjacent to the channel opening 42. The tip 30 further comprises a nozzle 48 extending from a back wall surface 50 of the cutout 40. The nozzle 48 allows a stream of water, air, or the like to be sprayed towards the outer surface of the objective lens 44 to clean the lens surface.

FIGS. 1c and 2 further illustrate the elevator 43 comprising a grasping slot 91 in accordance with one embodiment of the present invention. The grasping slot may take on any suitable shape or form for grasping of a medical device. In this embodiment, the grasping slot 91 is narrowly formed by inner sides 94 that define the grasping slot 91 formed through the elevator 43. Preferably, the grasping slot 91 is centrally formed through the elevator 43 for receiving a medical device (e.g., catheter or wire guide) and grasping the device during operation of the endoscope.

As depicted in FIG. 2, tip 30 further includes a guide catheter 112 and a wire guide 56 disposed through the guide catheter 112. The tip 30 further includes an elevator 43 configured to receive the guide catheter and/or wire guide for elevating the guide catheter 52 or wire guide 56. As will be described in greater detail below, the elevator 43 is comprised of polymeric material and has a grasping slot formed therethrough for enhanced grasping and reduced scraping purposes.

The elevator 43 is pivotally attached to the tip 30 and is configured to receive the medical instrument (e.g., catheter or wire guide) for elevating the medical instrument. As shown in FIG. 3, the distal tip houses the elevator 43 in channel opening 42. The elevator 43 is used to orient medical instruments such as a catheter. As discussed in greater detail below, this is accomplished by engaging the medical instrument and pivoting away from the distal tip thereby laterally moving the distal end of the medical instrument away from the distal tip. The elevator 43 thus secures the distal end of the medical instrument relative to the endoscope. That is, as the medical instrument is received in slot 91 of the elevator 43, the medical instrument laterally moves relative to the tip 30 when the elevator 43 pivots therefrom.

FIG. 3 illustrates that the endoscope tip 30 includes a cuff 60 as the main body of the tip 30, and a sleeve or cover 62 that covers the perimeter of the cuff 60. As shown, the cover 62 is formed using a nonconductive member such as any suitable polymeric material, e.g., high density polyethylene or polypropylene. In this embodiment, the cover 62 is attached to the cuff 60 by any suitable means, e.g., by adhesive bonding. The cuff 60 is disposed adjacent the working channel 63, which acts as a passageway for the insertion of the medical instrument, e.g., wire guide or catheter. In this embodiment, a channel 67 (FIG. 1c) is formed through the tip 30 such that the tip opening of the treatment instrument is able to be disposed through channel opening 42.

FIG. 3 further illustrates an elevator wire 90 connected to the elevator 43. In this embodiment, the elevator wire 90 is located at the operating portion 25 and extends through a guide tube 92 and a guide pipe 93 connected to the guide tube 92. The elevator wire 90 is in mechanical communication with the control system 14 so that manipulations at the control system 14 result in movement of the elevator wire 90 relative to the endoscope. FIG. 3 depicts (in phantom) movement of the elevator 43 when the elevator wire 90 is actuated at the control system 14, moving the position of the elevator 43 about the elevator turning support 68 as the elevator wire 90 is retracted or pulled.

Figure 4:
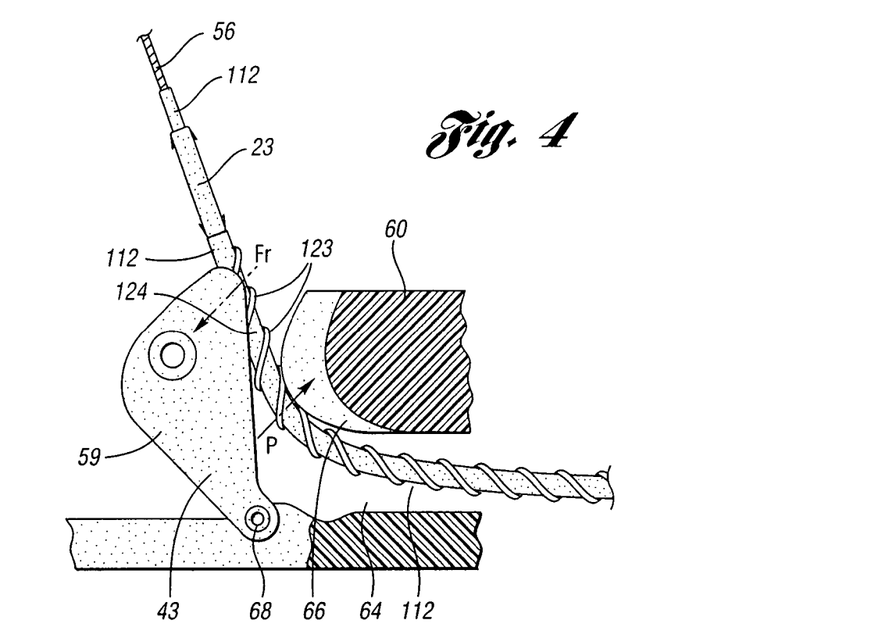
FIG. 4 is a cross-sectional view of the tip of the endoscope of FIG. 1, depicting a wire guide secured by an elevator.

In this embodiment, the elevator 43 is moved about the elevator turning support 68 by manipulating or actuating the control system 14 to pull or retract the elevator wire 90. As shown in FIG. 4, the result moves the wire guide 56 in the direction of the arrow P and pushes the elevator 43 against the cuff 60. Because the wire guide 56 is formed from a relatively axially stiff material, it tends to remain straight when pushed against the cuff 60, creating a reactive force in the direction of the arrow Fr in FIG. 4. By means of this reactive force, the wire guide 56 is pressed against the slot 91. Moreover, as the elevator 43 and the cuff 60 press against one another, the wire guide is secured.

Figure 5:
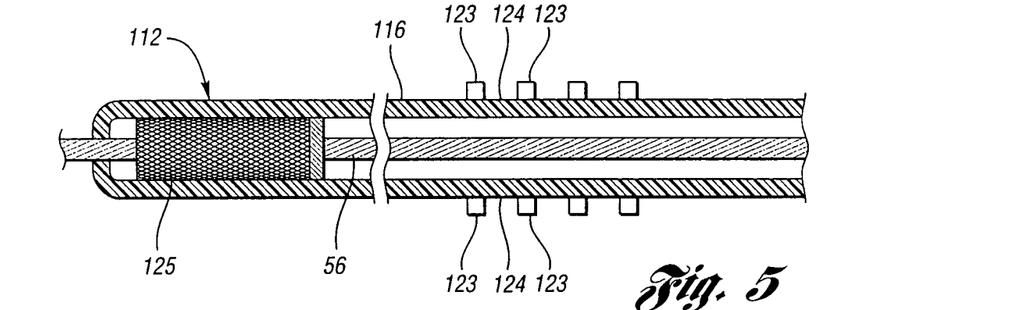
FIG. 5 is a side view of a portion a delivery apparatus in accordance with one embodiment of the present invention.
Figure 6:
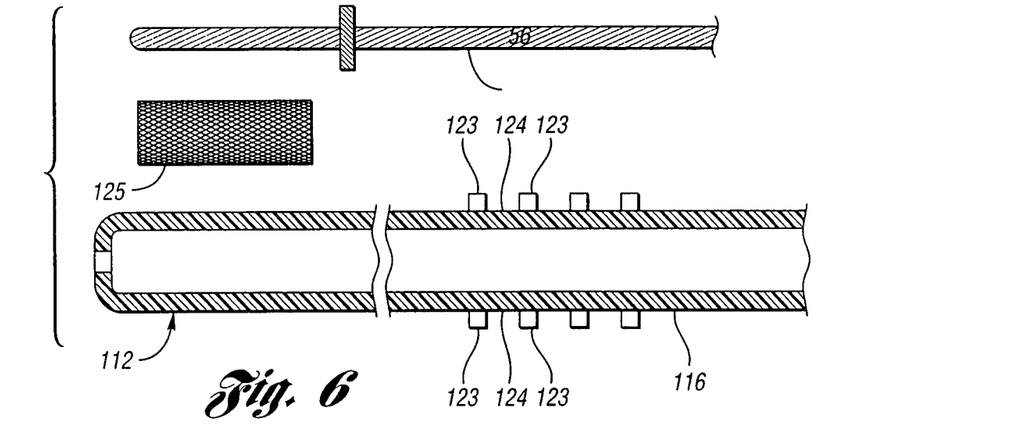
FIG. 6 is an exploded view of the delivery apparatus of FIG. 5.

FIG. 5 illustrates the pusher wire guide 56 about which an outer catheter 112 is disposed for deploying a medical device 125. As shown, the outer catheter 112 is configured to be coaxially disposed about the wire guide 56 and through the insertion tube 12 of the endoscope 11 for treatment of a patient. As shown in FIGS. 5 and 6, the outer catheter 112 includes an outer surface 116 having lateral or radial projections 123 formed thereon. As mentioned above, a pair of radial projections 123 define an anchor area 124 in which the inner side 94 of the elevator 43 may be received. When the elevator 43 is received in the anchor area 124, the catheter 112 is temporarily longitudinally fixed so that other devices (e.g., a wire guide) may be moved relative thereto. In this embodiment, each of the projections 123 is formed laterally along the outer surface 116 of the outer catheter 112. In this embodiment, the projections 123 extend integrally from the outer surface 116. However, it is to be understood that each projection 123 may extend radially in spatial segments so long as anchoring area 124 is able to receive the elevator 43 therein to longitudinally seat the catheter 112. Additionally, the projections 123 may extend radially in spatial segments in a staggered configuration or in an aligned configuration without falling beyond the scope or spirit of the present invention.

Each projection may be made of any suitable polymeric material. The polymeric material may include one of the following components: polytetrafluoroethylene, nylon, polyimide, polyamide, polyethylene, polypropylene, perfluoroelastomer, fluoroelastomer, nitrile, neoprene, polyurethane, silicone, styrene-butadiene, rubber, and polyisobutylene.

In one embodiment, each of the projections 123 is configured to distally fold at a pivot point when the outer catheter 112 is retracted and when a predetermined amount of force, "folding force," is applied by the elevator on a projection, causing the projection to distally bend or fold. Thus, in this embodiment, the folding force is a barrier force that allows the projections 123 to temporarily maintain the catheter 112 in a longitudinal position while another device (e.g., a wire guide or push wire) may be retracted or introduced. Moreover, the folding force is relatively easily reached when the clinician retracts or moves forward the catheter 112, thereby folding or bending the projections 123 to allow longitudinal movement.

Preferably, the projections 123 defines the anchor areas 124 to each have a shape that is cooperable with the shape of the inner side 94 (shown in FIG. 2) of the elevator 43 for lateral stability of the catheter and self-orientation of other medical devices, e.g., wire guide. Thus, as the elevator 43 is seated in an anchor area 124, the catheter 112 is held therein and the clinician is able to precisely move the wire guide 56 distally therethrough within the patient.

Figure 7A:
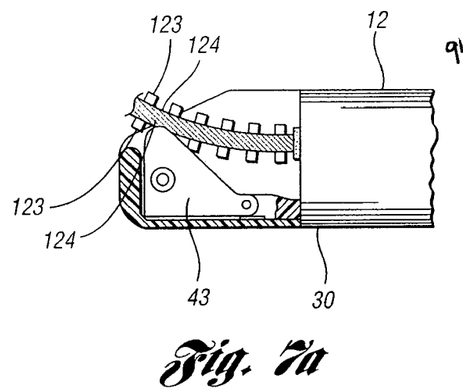
FIGS. 7a and 7b are side and perspective views of the delivery apparatus of FIG. 5 implemented with an endoscope.
Figure 7B:
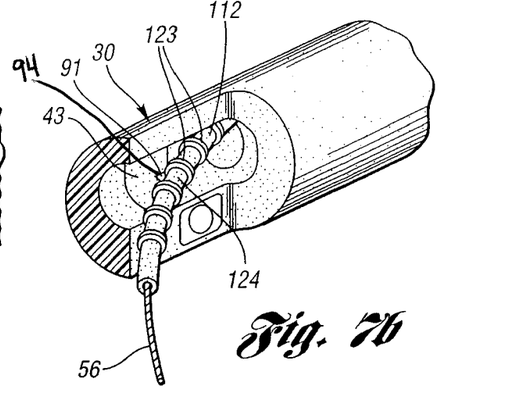

FIGS. 7a and 7b depict the outer catheter 112 and wire guide 56 within the distal tip 30 of endoscope 11. As shown, the projections 123 receive the inner side 94 in the anchor area 124. The projections 123 fold when the elevator 43 pushes against a projection 123 when the catheter 112 is retracted.

Figure 8:
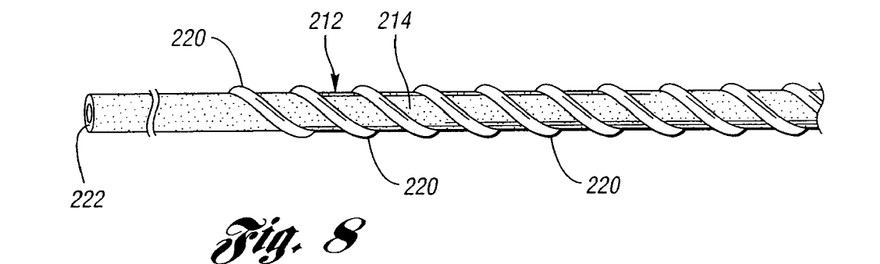
FIG. 8 is a side view of a distal portion of a catheter in accordance with another embodiment of the present invention.

In another embodiment, FIG. 8 illustrates inner catheter 212 in accordance with one embodiment of the present invention. As shown, the inner catheter 212 includes an outer surface 214 having a rotary member 220 formed thereon. In this embodiment, the rotary member 220 is helically formed from the distal tip 222 of the inner catheter and extends proximally therefrom. In this embodiment, the rotary member 220 is formed on the outer surface 214 of the catheter 212 having a first predetermined shape. Preferably, the rotary member 220 is spaced sufficiently away from the distal tip, e.g., 5-15 centimeters. The grasping slot 91 of the elevator 43 has a second predetermined shape cooperable with the first predetermined shape thus, the rotary member fits snug within the grasping slot 91 to seat the catheter therein. The rotary member may be made of any suitable material such as polymeric material, e.g., polytetrafluoroethylene, polyethylene, polypropylene, perfluoroelastomer, fluoroelastomer, nitrile, neoprene, polyurethane, silicon, styrene-butadiene, rubber, and polyisobutylene The helical formation of the rotary member 220 allows the catheter to seat within the grasping slot of the elevator and to be incrementally rotated, thereby allowing incremental longitudinal movement of the catheter relative to the endoscope. The rotary member is preferably integrally formed on the outer surface of the inner catheter. This may be accomplished by any suitable means such as extrusion. Alternatively, the rotary members may be attached onto the outer surface of the inner catheter by any suitable means, e.g., thermal bonding, sonic bonding, adhesive bonding.

Figure 9A:
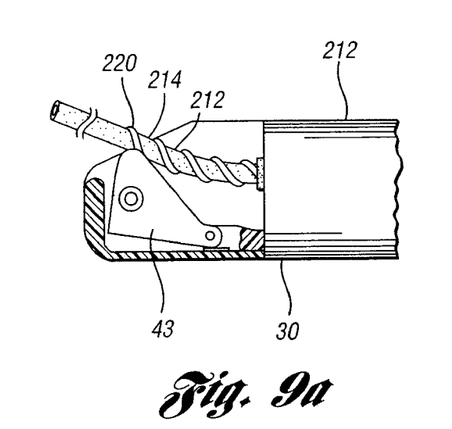
FIGS. 9a and 9b are side and perspective views of an endoscopic apparatus including the catheter of FIG. 8.
Figure 9B:
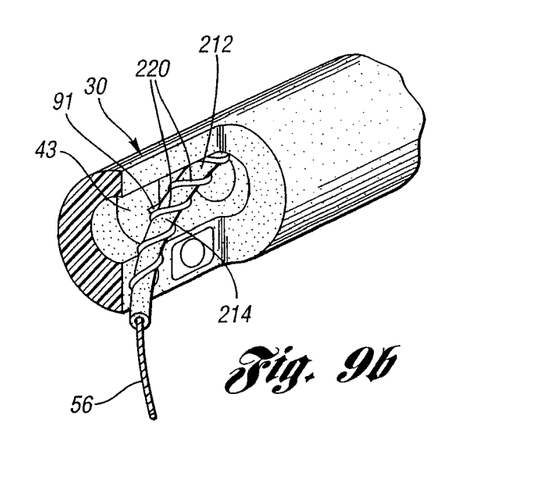

FIGS. 9a and 9b depict the inner catheter in contact with the elevator of the endoscope. As shown, the inner catheter is received preferably by the grasping slot and is seated therein such that axial or longitudinal movement of the inner catheter results in rotation of the inner catheter. Rotation of the inner catheter results in incremental longitudinal movement of the catheter for precise and controlled delivery of the inner catheter. In use, the elevator is preferably actuated to move the elevator away from the distal tip of the endoscope, thereby engaging and/or moving the inner catheter. In the event that additional longitudinal movement is needed, the clinician may further rotate the catheter so as to move the catheter distally. As a result, the rotational movement of the inner catheter results in longitudinal axial movement as desired. Alternatively, and particularly if precise or small movements are not needed, the clinician may disengage the elevator from the catheter to allow the catheter to be advanced or retracted without rotating the catheter.

Figure 10:
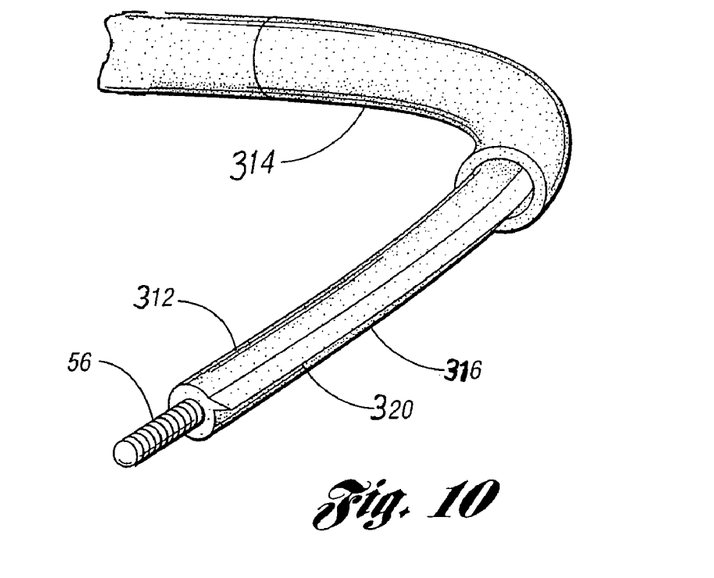
FIG. 10 is a perspective view of a catheter having a self-orienting rib in accordance with yet another embodiment of the present invention.

In yet another embodiment, FIG. 10 illustrates the wire guide 56 about which a catheter 312 and an outer sheath 314 are disposed. As shown, the outer sheath 314 is cooperable with the catheter 312. The inner catheter 312 and the outer sheath 314 are configured to be coaxially disposed about the wire guide 56 and through the insertion tube 12 of the endoscope 11 for treatment of a patient. As shown in FIG. 11, the catheter 312 includes an outer surface 316 having self-orienting rib or ridge 320 formed thereon. In this embodiment, the ridge 320 is formed longitudinally along the outer surface 316 of the catheter 312.

Preferably, the ridge 320 is formed of a shape that is cooperable with the shape of the grasping slot 91 (shown in FIGS. 1c and 2) of the elevator 43 for self-orientation. Thus, as the ridge 320 is seated in the grasping slot 91, the catheter 312 is held within the grasping slot 91. This allows the clinician to be able to longitudinally advance or retract the catheter 312 without radially changing the position of the catheter 312, e.g., during a sphincterotomy, within the patient anatomy.

Figures 11A, 11B:
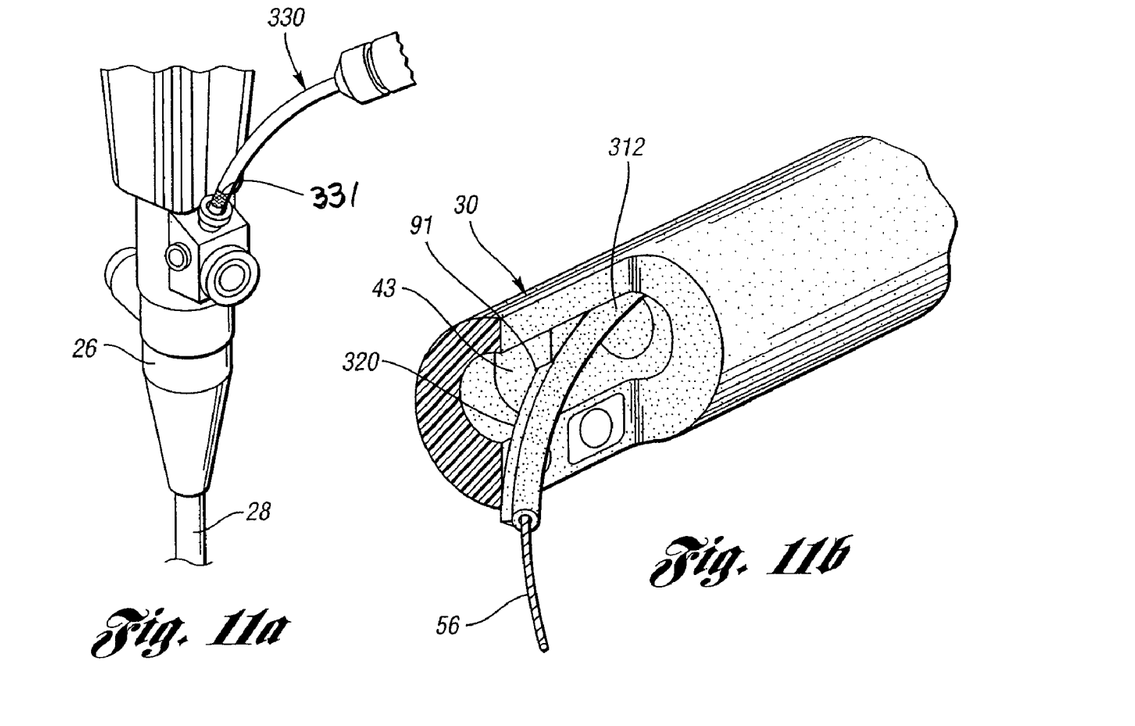
FIGS. 11a and 11b are elevated views of the catheter having an indicator marker for assessment thereof relative to the endoscope.

FIGS. 11a and 11b depict a delivery system 330 of the inner catheter 312 and wire guide 56. As shown, an indicator marker 331 is disposed on the proximal portion of the catheter 312. As shown, an indicator marker 331 is disposed on the proximal portion of the catheter 312 to indicate the location of the distal end of the inner catheter 312 relative to the elevator 43. In this example, the indicator marker 331 is disposed about the inner catheter 312 to indicate that the device is withdrawn far enough to permit direct engagement of the wire guide with the elevator 43.

However, in another example, the indicator marker 331 may be disposed about the inner catheter 312 to indicate that the distal end of the inner catheter is withdrawn far enough to permit seating of the ridge (mentioned above) on the elevator 43. Of course, the indicator marker may be placed on any other component of the delivery system 330 to indicate other positions of the inner catheter. The indicator marker 331 may be disposed about the inner catheter by any suitable means, e.g., adhesive bonding or inking.

Figure 12:
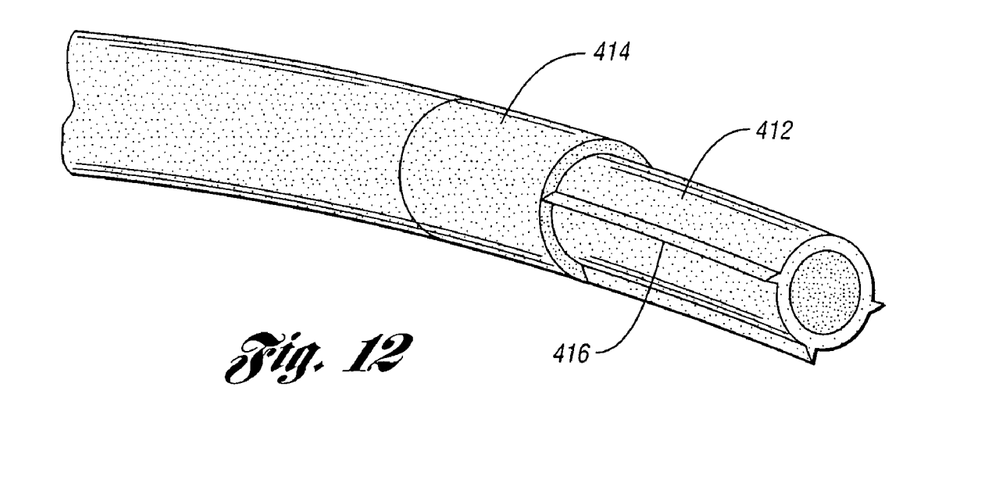
FIG. 12 is an elevated view of the inner catheter in accordance with still another embodiment of the present invention.

FIG. 12 illustrates a shouldered catheter 412 and an outer sheath 414 disposed about the shouldered catheter 412. As shown, the shouldered catheter comprises three ribs 416 formed longitudinally therealong. In this embodiment, each rib 416 is spaced about 90 degrees from at least one other rib 416. Preferably, the ribs 416 are used for indexing through 180 degrees of rotation. However, the ribs 416 may be spaced between each other in any other suitable manner, e.g., evenly or unevenly, without falling beyond the scope or spirit of the present invention. As shown, the outer sheath 414 is cooperable with the shouldered catheter 412. The shouldered catheter 412 and the outer sheath 414 are configured to be coaxially disposed about a wire guide and through the insertion tube of the endoscope for treatment of a patient.

As in other embodiments, the ribs 416 have a shape cooperable with the shape of the grasping slot of the elevator for self-orientation. Thus, as the rib is seated in the grasping slot, the shouldered catheter is held therein and the clinician is able to precisely move the guide wire distally therethrough within the patient. Due to the cooperable shape of the rib relative to the grasping slot, the clinician merely retracts the inner catheter to withdraw from the patient. In this embodiment, when a rotation is needed during use of the device, the clinician merely rotates the shouldered catheter, disengaging one rib from the grasping slot. At a 90-degree turn, another rib is mated within the grasping slot. Thus, the clinician is provided a mating contact feel, indicating that a 90-degree (or 180-degree) turn has been completed.

Figure 13:
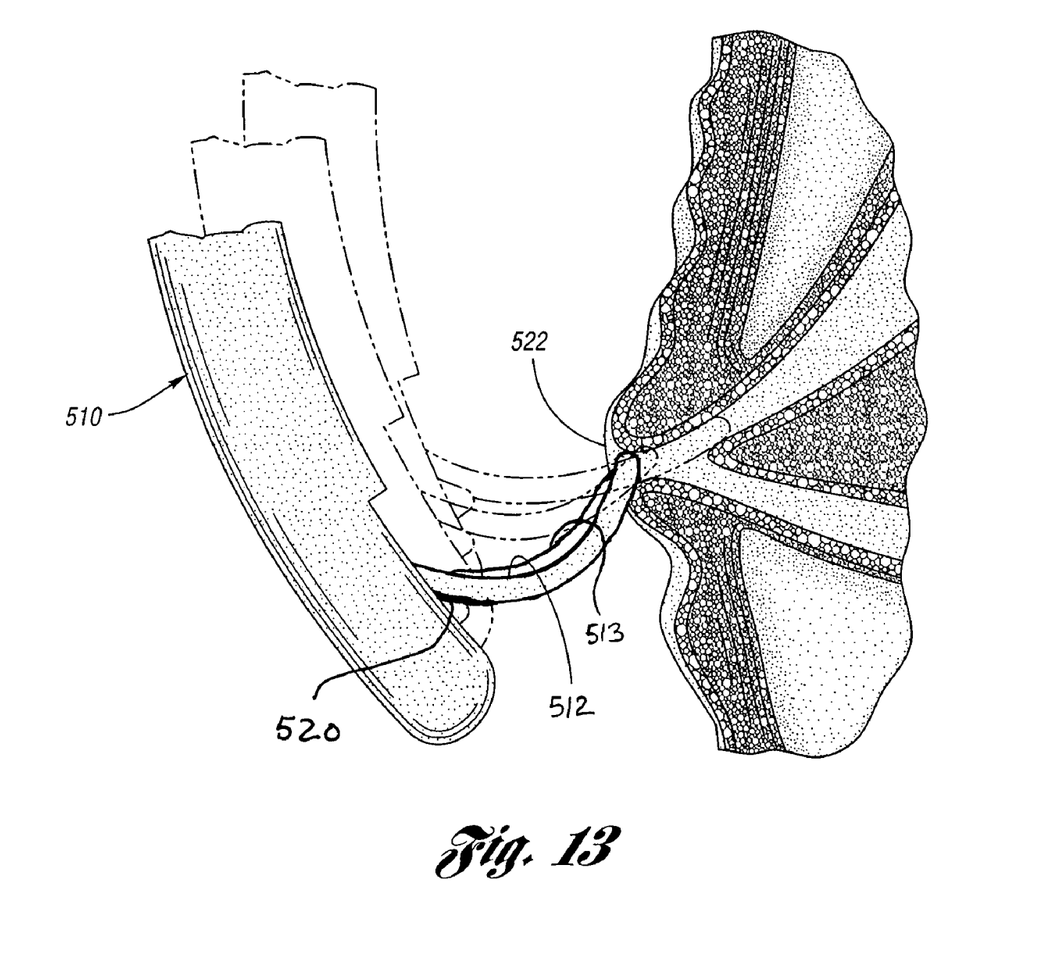
FIG. 13 is an environmental side view of a sphincterotome having a self-orienting ridge in accordance with yet another embodiment of the present invention.

FIG. 13 illustrates an endoscope 510 having a sphincterotome 512 that includes a sphincterotome wire 513 and a self-orienting ridge 520 formed longitudinally thereon in accordance with one embodiment of the present invention as similarly shown in FIG. 10. As shown in the bowing technique used, the endoscope is positioned under the papilla. By bowing the sphincterotome, the superior margin of the papillary orifice 522 is approached from below in the attempt to push the sphincterotome into the common bile duct. After cannulating the bile duct with the sphincterotome, the sphincterotome is advanced inside the bile duct. The entire length of the exposed wire should be beyond the intramural segment. Its position in the common bile duct is reaffirmed by contrast instillation. The spincterotome is then slowly withdrawn.

As the wire 513 becomes visible outside the papillary orifice, the sphincterotome wire is slowly tightened to a partially flexed position by proximal manipulation of the sphincterotome. As it is received in the grasping slot of the elevator, the self-orienting ridge 520 maintains the sphincterotome wire and catheter 512 positioned at the 12 o'clock position of the papillary orifice. This avoids injury to the duodenal wall or pancreatic duct.

The embodiments of the present invention discussed herein may be used with the embodiments discussed in the U.S. Non-Provisional Application filed on Mar. 5, 2007 entitled "ENDOSCOPIC ELEVATOR APPARATUS." Such application claims the benefit of U.S. Provisional Application Ser. No. 60/779,182, filed on Mar. 3, 2006, entitled "ENDOSCOPIC ELEVATOR APPARATUS HAVING A POLYMERIC ELEVATOR WITH A GRASPING SLOT" and U.S. Provisional Application Ser. No. 60/779,181, filed on Mar. 3, 2006, entitled "ENDOSCOPE HAVING AN ELEVATOR WITH A GRASPING COVER," the entire contents of each are incorporated herein by reference.

While the present invention has been described in terms of preferred embodiments, it will be understood, of course, that the invention is not limited thereto since modifications may be made to those skilled in the art, particularly in light of the foregoing teachings.

The invention claimed is:

1. A delivery apparatus cooperable with a grasping slot of an elevator of an endoscope for delivery to a target location in a patient, the apparatus comprising:
    a catheter including an inner lumen and an outer surface having a projection formed thereon, the projection radially extending from the outer surface and having a first predetermined shape, the first predetermined shape being cooperable with a second predetermined shape of the grasping slot such that the projection is configured to engage the elevator and fit snugly within the grasping slot to temporarily maintain at least one of a longitudinal position and a radial position of the delivery apparatus; and
    an elongate member disposed through the inner lumen of the catheter and extending through an open distal end of the catheter.

2. The apparatus of claim 1 wherein the projection is a plurality of projections.

3. The apparatus of claim 1 wherein the projection is at least one pair of projections circumferentially formed on the outer surface in longitudinal relationship with and spaced apart from each other, the at least one pair of projections radially extending from the outer surface of the catheter, the at least one pair of projections defining an anchor area in which the elevator is to be received for temporary longitudinal fixation of the catheter.

4. The apparatus of claim 3 wherein the catheter includes a distal portion and a distal end extending therefrom, the projections being formed at the distal portion and being proximally spaced from the distal end.

5. The apparatus of claim 3 wherein each of the projections has a pivot point about which to fold when pressed against the elevator upon retraction of the catheter.

6. The apparatus of claim 1 wherein the projection is a rotary member formed helically on the outer surface, the rotary member being cooperable with the grasping slot of the elevator, wherein rotation of the catheter within the grasping slot incrementally moves the catheter relative to the target location.

7. The apparatus of claim 6 wherein the catheter includes a distal portion and a distal end extending therefrom, the rotary member being disposed on the distal portion and being spaced from the distal end.

8. The apparatus of claim 7 wherein the rotary member is disposed only on the distal portion.

9. The apparatus of claim 1 wherein the projection is a self-orienting ridge formed longitudinally along the outer surface of the catheter, the self-orienting ridge being cooperable with the grasping slot of the elevator, the ridge being configured to be received in the grasping slot to inhibit rotation of the catheter with respect to the elevator.

10. The apparatus of claim 9 wherein the catheter includes a distal portion and a distal end extending therefrom, the ridge being formed on the distal portion and being spaced from the distal end.

11. The apparatus of claim 10 wherein the self-orienting ridge is a plurality of self-orienting ridges.

12. The apparatus of claim 1 wherein the catheter has a distal portion and a proximal portion, the proximal portion having an indicator marker disposed thereon for identifying the location of the catheter during endoscopy.

13. An endoscopic system having enhanced features for delivering a medical device in a patient, the system comprising:
    an insertion tube extending to a distal tip including an elevator movably attached thereto, the elevator having an inner side formed thereon defining a grasping slot having a second predetermined shape;
    a catheter including an inner lumen and an outer surface having a projection formed thereon, the projection radially extending from the outer surface and having a first predetermined shape, the projection being configured to engage the elevator such that the projection fits snugly within the grasping slot, wherein the first and second predetermined shapes of the projection and the grasping slot work together to temporarily maintain at least one of a longitudinal position and a radial position of the catheter; and an elongate member disposed through the inner lumen of the catheter and extending through an open distal end of the catheter.

14. The system of claim 13 wherein the projection is at least one pair of projections circumferentially formed on the outer surface in longitudinal relationship with each other, the at least one pair of projections radially extending from the outer surface of the catheter, the at least one pair of projections defining an anchor area in which the elevator is to be received for temporary longitudinal fixation of the catheter.

15. The system of claim 13 wherein the projection is a rotary member formed helically on the outer surface, the rotary member being cooperable with the grasping slot for the elevator, wherein rotation of the catheter within the grasping slot incrementally moves the catheter relative to the target location.

16. The system of claim 13 wherein the projection is a self-orienting ridge formed longitudinally along the outer surface of the catheter, the self-orienting ridge being cooperable with the grasping slot of the elevator, the ridge being configured to be received in the grasping slot to inhibit rotation of the catheter with respect to the elevator.

* * * * *

UNITED STATES PATENT AND TRADEMARK OFFICE
CERTIFICATE OF CORRECTION

PATENT NO. : 8,109,872 B2  
APPLICATION NO. : 11/713940  
DATED : February 7, 2012  
INVENTOR(S) : Kenneth C. Kennedy, II et al.

It is certified that error appears in the above-identified patent and that said Letters Patent is hereby corrected as shown below:

On the Title Page

In the left column, after item (65), insert item (63):

--Related U.S. Application Data

This application claims benefit of Application No. 60/778,813, filed on March 3, 2006, and claims benefit of Application No. 60/779,244, filed on March 3, 2006, and claims benefit of Application No. 60/779,549, filed on March 6, 2006.--

Signed and Sealed this  
Twenty-fourth Day of April, 2012

David J. Kappos  
*Director of the United States Patent and Trademark Office*